United States Patent
Busch et al.

(10) Patent No.: US 9,855,242 B2
(45) Date of Patent: Jan. 2, 2018

(54) COMPOSITION FOR AN IMMUNOMODULATION

(71) Applicant: Eberhard Karls Universität Tübingen Medizinische Fakultät, Tuebingen (DE)

(72) Inventors: Christian Busch, Winterthur (CH); Sascha Venturelli, Todtmoos (DE)

(73) Assignee: EBERHARD KARLS UNIVERITÄT TÜBINGEN MEDIZINISCHE FAKULTÄT, Tuebingen (DE)

( * ) Notice: Subject to any disclaimer, the term of this patent is extended or adjusted under 35 U.S.C. 154(b) by 0 days.

(21) Appl. No.: 15/130,556

(22) Filed: Apr. 15, 2016

(65) Prior Publication Data

US 2016/0303070 A1    Oct. 20, 2016

Related U.S. Application Data

(63) Continuation of application No. PCT/EP2014/071971, filed on Oct. 14, 2014.

(30) Foreign Application Priority Data

Oct. 16, 2013 (DE) .................. 10 2013 017 165

(51) Int. Cl.
| | | |
|---|---|---|
| A61K 31/335 | (2006.01) | |
| A61K 31/353 | (2006.01) | |
| A23L 33/10 | (2016.01) | |
| A61K 9/107 | (2006.01) | |

(52) U.S. Cl.
CPC ............ A61K 31/353 (2013.01); A23L 33/10 (2016.08); A61K 9/1075 (2013.01); *A23V 2002/00* (2013.01)

(58) Field of Classification Search
USPC ........................................................ 514/449
See application file for complete search history.

(56) References Cited

U.S. PATENT DOCUMENTS

| | | | | |
|---|---|---|---|---|
| 6,399,579 B1 * | 6/2002 | Lenoble | ............... | A61K 31/00 424/725 |
| 2005/0032882 A1 * | 2/2005 | Chen | ................... | A61K 31/352 514/456 |
| 2008/0031986 A1 | 2/2008 | Tripp et al. | | |
| 2016/0067211 A1 | 3/2016 | Busch et al. | | |

FOREIGN PATENT DOCUMENTS

| | | |
|---|---|---|
| DE | 20 2009 016 292 U1 | 5/2011 |
| DE | 10 2013 104 342 A1 | 10/2014 |
| EP | 1 543 834 A1 | 6/2005 |
| EP | 1 698 332 A1 | 9/2006 |
| WO | WO 02/39960 A2 | 5/2002 |
| WO | WO 2011/066937 A1 | 6/2011 |

OTHER PUBLICATIONS

Zhao et al. J. Nat. Prod., 2005, 68(1): 43-49.*
Albini, et al. 2006 "Mechanisms of the antiangiogenic activity by the hop flavonoid xanthohumol: NF-κb and Akt as targets" *The FASEB Journal* 20: 527-529.
Brunelli, et al. 2007 "8-prenylnaringenin, inhibits estrogen receptor-α mediated cell growth and induces apoptosis in MCF-7 breast cancer cells" *Journal of Steroid Biochemistry & Molecular Biology* 107: 140-148.
Brunelli, et al. 2008 "8-prenylnaringenin inhibits epidermal growth factor-induced MCF-7 breast cancer cell proliferation by targeting phosphatidylinositol-3-OH kinase activity" *Journal of Steroid Biochemistry and Molecular Biology* 113(3-5): 163-170.
Cho, et al. 2010 "Xanthohumol inhibits IL-12 production and reduces chronic allergic contact dermatitis" *International Immunopharmacology* 10: 556-561.
Cidade, et al. 2001 "Artelastocarpin and Carpelastofuran, Two New Flavones, and Cytotoxicities of Prenyl Flavonoids from *Artocarpus elasticus* against Three Cancer Cell Lines" *Planta Med* 67: 867-870.
Delmulle, et al. 2006 "Anti-proliferative properties of prenylated flavonoids from hops (*Humulus lupulus* L.) in human prostate cancer cell lines" *Phytomedicine* 13: 732-734.
Delmulle, et al. 2008 "Treatment of PC-3 and DU145 Prostate Cancer Cells by Prenylflavonoids from Hop (*Humulus lupulus* L.) induces a Caspase-independent Form of Cell Death" *Phytother Res.* 22(2): 197-203.
Diller, et al. 2007 "Ability of Prenylflavanones Present in Hops to Induce Apoptosis in a Human Burkitt Lymphoma Cell Line" *Planta Med* 73(8): 755-761.
Gao, et al. 2009 "Immunomodulatory activity of xanthohumol: inhibition of T cell proliferation, cell-mediated cytotoxicity and Th1 cytokine production through suppression of NF-κB" *Immunopharmacol Immunotoxicol.* 31(3): 477-484.
German Examination Report for Case No. 10 2013 017 165.2 dated Sep. 4, 2014 (in 8 pages).
German Court Decision Jan. 29, 1988 14W(Pat) 46/85, BPatG (in 3 pages).
Gester, et al. 2001 "An efficient synthesis of the potent phytoestrogens 8-prenylnaringenin and 6(1,1-dimethylallyl)naringenin by europium(III)-catalyzed Claisen rearrangement"*Tetrahedron* 57: 1015-1018.
Gredel, et al. 2008 "Phytoestrogens and phytoestrogen metabolites differentially modulate immune parameters in human leukocytes" *Food and Chemical Toxicology* 46: 3691-3696.
Hodek, et al. 2002 "Flavonoids-potent and versatile biologically active compounds interacting with cytochromes P450" *Chemico-Biological Interactions* 139: 1-21.
International Search Report for International Application PCT/EP2014/071971, dated Jan. 9, 2015 (in 12 pages).
Kim, et al. 2002 "Effects of Sophoraflavanone G, a Prenylated Flavonoid from *Sophora flavescens*, on Cyclooxygenase-2 and In Vivo Inflammatory Response" *Arch Pharm Res* 25(3): 329-335.

(Continued)

*Primary Examiner* — Rei-Tsang Shiao
(74) *Attorney, Agent, or Firm* — Knobbe, Martens, Olson & Bear, LLP

(57) ABSTRACT

The present invention relates to a composition for the immunomodulation and uses and methods associated therewith.

11 Claims, 10 Drawing Sheets

(56) References Cited

OTHER PUBLICATIONS

Kuete, et al. 2011 "Cytotoxicity and mode of action of four naturally occurring flavonoids from the Genus *Dorstenia*: Gancaonin Q, 4-hydroxylonchocarpin, 6-prenylapigenin, and 6,8-diprenyleriodictyol" *Planta Med* 77: 1984-1989.

Li, et al. 1991 "In vitro immunopharmacological profile of the plant flavonoid baohuoside-1" *Int J Immunopharmac* 13(2/3): 129-134.

Milligan, et al. 1999 "Identification of a potent phytoestrogen in hops (*Humulus lupulus* L.) and beer" *The Journal of Clinical Endocrinology & Metabolism* 83(6): 2249-2252.

NF-κB definition from Wikipedia, available online at: en.wikipedia.org/wiki/NF-κB, downloaded Sep. 17, 2014 (in 19 pages).

Peluso, et al. 2010 "Xanthohumol and related prenylated flavonoids inhibit inflammatory cytokine production in LPS-activated THP-1 monocytes: Structure-activity relations and In Silico binding to myeloid differentiation protein-2 (MD-2)" *Planta Med* 76: 1536-1543.

Pepper, et al. 2004 "8-Prenylnaringenin, a Novel Phytoestrogen, Inhibits Angiogenesis In Vitro and In Vivo" *Journal of Cellular Physiology* 199: 98-107.

Rong, et al. 2001 "8-Prenylnaringenin, the phytoestrogen in hops and beer, upregulates the function of the E-cadherin/ catenin complex in human mammary carcinoma cells" *European Journal of Cell Biology* 80: 580-585.

Son, et al. 2007 "Pomiferin, histone deacetylase Inhibitor isolated from the fruits of *Maclura pomifera*" *Bioorganic & Medicinal Chemistry Letters* 17: 4753-4755.

Tischer, et al. 2007 "Selective C-6 Prenylation of Flavonoids via Europium(III)—Catalyzed Claisen Rearrangement and Cross-Metathesis" *Adv. Synth Catal* 349: 147-151.

Wesolowska, et al. 2010 "8-Prenylnaringenin is an inhibitor of multidrug resistance-associated transporters, P-glycoprotein and MRP1" *European Journal of Pharmacology* 644: 32-40.

Wun, et al. 2013 "Anti-inflammatory effect of sophoraflavanone G isolated from *Sophora flavescens* in lipopolysaccharide-stimulated mouse macrophages" *Food and Chemical Toxicology* 62: 255-261.

Zhang, et al. 1998 "Daidzein and Genistein Glucuronides In Vitro Are Weakly Estrogenic and Activate Human Natural Killer Cells at Nutritionally Relevant Concentrations" *J Nutr* 129: 399-405.

\* cited by examiner

A    6-PN

B    8-PN

A

Control

6-PN 25 µM

8-PN 25 µM

B

A

B

COMPOSITION FOR AN IMMUNOMODULATION

CROSS-REFERENCES TO RELATED APPLICATIONS

This application is a continuation of copending international patent application PCT/EP2014/071971 filed on 14 Oct. 2014 and designating the U.S., which has been published in German, and claims priority from German patent application DE 10 2013 017 165.2 filed on 15 Oct. 2013. The entire contents of these prior applications are incorporated herein by reference.

FIELD

The present invention relates to a composition for an immunomodulation and uses and methods associated therewith.

BACKGROUND

Immunotherapies are forms of treatment where the immune system of an organism is influenced. The immunomodulation may serve for an attenuation of the immune system such as after transplantations and to avoid a rejection reaction, but also for an immunostimulation, i.e. an enhancement of the natural immune response. The active agents of an immunotherapy are generally identified as immunomodulators. Immunomodulators may be, therefore, immunostimulants or immunoinhibitors. An example of a prominent immunostimulant is the interferon which is used in the therapy of hepatitis C diseases. Also plant-based immunomodulators are described, for example extracts from the hemp plant or the purple cone flower.

For the malign melanoma already different immunomodulating substances exist which are used in the clinic and which modulate the activity of the natural killer cells (NK cells). Therefore, for such purpose interferon α is used in the adjuvant melanoma therapy in the stages II and III or interleukin 2 (IL-2) is used in the treatment of the metastasizing melanoma in the stage IV.

Also in other diseases immunomodulating substances are used, for example pegylated interferon for the treatment of hepatitis C or interferon β for the treatment of multiple sclerosis.

The immunomodulating substances used so far did mostly not prove successful in practice. This applies especially for the melanoma therapy. There the immunotherapies so far executed mostly only show moderate response rates of less than 10% and simultaneously significant side effects, for example medicament-induced cases of death in systemic IL-2 therapies in stage IV. Also in fields of infections or autoimmune diseases the currently approved therapies result in significant problems. Despite intensive immunotherapy chronic processes are still the rule, such as for example in hepatitis C or the multiple sclerosis.

In addition, many of the currently used immunomodulators are expensive in their production. They require complex syntheses and purification methods, so finally the provision of larger amounts requires larger investments also for the patient.

SUMMARY

Against this background it is a problem of the present invention to provide a new immunomodulator by means of which the problems described in the prior art can be avoided or at least reduced.

This problem is solved by the provision of a composition comprising as an active agent an prenylflavonoid, preferably prenylnaringenin (PN).

Prenylflavonoids belong to the group of flavonoids, a large group of lower molecular polyphenolic compounds. Flavonoids can be found in plants and consist of flavones, flavonoles, flavonones, flavan-3-ols, and anthocyanines. These secondary plant metabolites play a role in the defense of the plant against microorganisms or fungi and in the protection against oxidative stress.

An important representative of the prenylflavonoids is the prenylnaringinin (PN).

The inventors were able to demonstrate in cell culture in an impressive manner that prenylflavonoids or prenylnaringinin cause a modulation of the immune system.

The prenylflavonoids or the prenylnaringinin and the specific compounds included herein according to the invention may be the only active agents in the sense of a monotherapy. However, further active agents can be provided which may result in synergistic effects.

The problem underlying the invention is herewith completely solved.

According to an embodiment of the invention, the composition comprises 6-prenylnaringinin (6-PN) and/or 8-prenylnaringinin (8-PN).

6-PN and 8-PN are so called prenylflavonoids. The can be found in low concentrations for example in hops and in beer. The structure of this class of flavonoids is derived from 2-phenylchrome-4-one. 6-PN and 8-PN are isomers. The difference lies in the position of the prenyl group consisting of five carbon atoms. 6-PN and 8-PN are products of a ring formation reaction of a common precursor molecule, desmethylxanthohumol, a polyphenol, which is based on the structure of 1,3-diphenyl-2-propene-1-one. Both molecules exist as enatiomeres (R,S).

8-PN has a strong binding affinity for estrogen receptors of the uterus of rats and has been identified as a potent phytoestrogen due to a characteristic spacing of the hydroxy groups, which imitate beta estradiol; see Milligan et al. (1999); Identification of potent phytoestrogen in hops (*Humulus lupulus* L.) and beer, J. Clin. Endocrinol. Metab. 84, 2249-2252.

Beside the antioxidative properties some flavonoids comprise anticancer properties; see Hodek et al. (2002) Flavonoids-potent and versatile biologically active compounds interacting with cytochromes p. 450, Chem. Biol. Interact. 139, 1-21. 8-PN inhibits the angiogenesis induced by the basic fibroblast growth factor and the vascular endothelial growth factor in a three dimensional collagen gel in vitro and in chorioallantois membrane assays in vivo; see Hepper et al. (2004), 8-Prenylnaringenin, A novel phytoestogen, inhibits angiogenesis in vitro and in vivo, J. Cell Physiol. 199, 98-107. 8-PN immitates the effects of 17β estradiol on the breast cancer cells MCF-7; see Rrong et al. (2001), 8-Prenylnaringenin, the phytoestrogen in hops and beer, upregulates the function of the e-cadherin-/catenin complex in human mammary carcinoma cells, Eur. J. Cell Biol. 80, 5 180-585. 8-PN induces furthermore the apoptosis in MCF7 cells and in a leukemia blast which is resistant against a large number of active agents; see Brunelli et al. (2007), 8-Prenylnaringenin, inhibits estrogen receptor-α mediated cell growth and induces apoptosis in MCF-7 breast cancer cells, J. Steroid. Biochem. Mol. Biol. 107, 140-148, and Diller et al. (2007), Ability of prenylflavanones present in hops to induce apoptosis in a human Burkitt lymphoma cell line, Planta Med. 73, 755-761. In addition, recently the inhibition of the P glycoprotein, the transporter protein associated with multi-resistance, and the inhibition of MRP1 by 8-PN was described; see Wesolowska et al. (2010), 8-Prenylnaringenin is an inhibitor of multidrug resistance-associated transporters, P-glycoprotein and MRP1, Eur. J. Pharmacol. 644, 32-40. Furthermore, 8-PN directly inhibits the activation of the PI (3) K/Akt signaling pathway in MCF-7 cells in vitro; Brunelli et al. (2009), 8-Prenylnaringenin inhibits epidermal growth factor-induced MCF-7 breast cancer cell proliferation by targeting phosphatidylinositol-3-OH kinase activity, J. Steroid. Biochem. Mol. Biol. 113, 163-170. 6-PN and 8-PN show antiproliferative effects on the human prostate cancer cell lines PC-3 and DU145 in vitro; Delmulle et al. (2006), Antiproliferative properties of prenylated flavonoids from hops (Humulus lupulus L.) in human prostate cancer cell lines, Phytomedicine 13, 732-734. This happens in the absence of a caspase-3 activation and typical apoptotic morphological characteristics; Delmulle et al. (2008), Treatment of PC-3 and DU145 prostate cancer cells by prenylflavonoids from hop (Humulus lupulus L.) induces a caspase-independent form of cell death, Phytother. Res. 22, 197-203.

In the non-disclosed Germany patent application DE 10 2013 104 342 the use of 6-PN and 8-PN is described for the treatment of a melanoma and a melanoma precursor of the skin as well as a mucosa metastasis. There it is also described that 6-PN and 8-PN are distinct inhibitors of histone deacetylases (HDACs) of classes I, II, and IV.

The suitability of 6-PN and 8-PN as an immunomodulator is so far not described in the state of the art.

The inventors could demonstrate in an impressive manner that 6-PN and 8-PN exert immunomodulatory effects on the innate immune system or on natural killer cells (NK cells), respectively. The prenylnaringinins massively increase the viability of NK cells, extend the overall survival of NK cells and cause an increased killing of altered cells such as virus infected or tumor cells. Thus, the prenylnaringinins activate directly or indirectly the NK cells.

Therefore, according to another embodiment of the invention the immunomodulation is an immunostimulation.

This measure has the advantage that via a targeted activation of the innate immune system a stimulation of the endogenous defense mechanisms is caused and, as a result, the organism is protected against diseases in an improved manner.

According to another embodiment the immunomodulation or immunostimulation is such of the innate immune system.

This measure has the advantage that it is acted on that part of the immune system in a positive manner via which a majority of infections and diseases can be defended.

According to another embodiment of the invention the immunomodulation causes a stimulation and/or an increase of the viability and/or an increase of the lifetime and/or an increase of the activity of the natural killer cells (NK cells).

This measure has the advantage that it is acted on the central cell type of the innate immune system in a modulating or stimulating way. As a result the body is strengthened and in the position to identify and kill abnormal cells, such as tumor cells or virus infected cells. In this regard, the activation of the NK cells may both result from the direct activation of the NK cells, e.g. by upregulation of stimulating mechanisms. Specific surface ligands or receptors on target cells, e.g. tumor or virus infected cells, can be upregulated, which can be identified by cells of the innate immune system and thus result in an increased activity.

Further, the activation of the NK cells may be caused by an indirect activation, e.g. by downregulating inhibitory mechanisms.

In another embodiment the composition according to the invention can be a pharmaceutical composition, which further may be configured for the treatment of a disease which is selected from the group consisting of viral infections, autoimmune diseases or tumor diseases.

It goes without saying that the pharmaceutical composition according to the invention may comprise a pharmaceutically acceptable formulation. Pharmaceutically acceptable formulations are well-known in the state of the art. As example it is referred to the treatise of Kibbe A. (2000), Handbook of Pharmaceutical Excipients, third edition, American Pharmaceutical Association and Pharmaceutical Press. The pharmaceutical composition according to the invention may further contain additives. These encompass any compound or composition which are beneficial for the use according to the invention, including salts, binders, solvents, dispersions, and further agents which are usually used in the formulation of medicines.

The compound according to the invention can be provided in an application form which allows a systemic or topical application, such as for example as an injection or drinkable solution, ointment, creme, lotion, gel, paste, transdermal therapeutic system, foam, powder. The active agent can also be encapsulated, for example in liposomes.

According to an alternative embodiment the composition according to the invention is a food product.

This measure has the advantage that the positive properties of the prenylflavonoids which were discovered by the inventors can be ingested through food. The provision of a medicament which must be synthesized in a complex manner and is to be approved is not necessary. The food product may contain the prenylflavonoid or 6-PN and/or 8-PN, respectively, in a naturally existing concentration. The food product may, however, be enriched with respect to these active agents which could result in an increased positive effect on the health state of the organism. The food product can be a liquid but also a solid foodstuff.

In an embodiment of the invention the food product is based on hops.

This measure has the advantage that a natural "raw material" is used for the prenylflavonoids or 6-PN and/or 8-PN which is available in large amounts and from which the active agents can be well-isolated or enriched, respectively.

In another embodiment of the composition according to the invention the active agent, i.e. the prenylflavonoid or prenylnaringinin (PN), preferred 6-PN and/or 8-PN, is present in micelled form or packaged into micelles.

Micelles, also referred to as association colloids, are aggregates of amphiphilic molecules or surface active substances, respectively, which spontaneously aggregate in a dispersion medium, e.g. water. In comparison to liposomes they comprise a significantly smaller diameter. In the average it is in the range of nanometers, between approx. 1 nm-approximately 100 nm, preferably between approx. 20 nm-80 nm, further preferably appr. 35 nm-65 nm, highly preferably approximately 30 nm or 50 nm. "Approx." means in this connection ±10%. The packaging of the active agent into micelles has the advantage that therewith the bioavailability in the organism is significantly increased. The micelles which contain the active agent are present in a solubilisate. The active agent is so to say "solubilized". It has become apparent that a packaging in such micelles is particularly suited which are provided by the company Aquanova, Darmstadt, Germany, under the name "product micelle". The obtained solubilisates are identified as NovaSOL®. The product micelles are thermally, mechanically and also in the gastric acid stable and comprise in the average a diameter of only approx. 30 nm.

A further subject matter of the present invention relates to the use of a prenylflavonoid, preferably of prenylnaringinin, further preferably of 6- and/or 8-prenylnaringinin, as an immunomodulator, preferably an immunostimulator, further preferably for the stimulation and/or to increase the viability and/or to increase the life span of the natural killer cells (NK cells).

A further subject matter of the present invention relates to a method for the immunomodulation, preferably for the immunostimulation, further preferably to the stimulation and/or to increase the viability and/or to increase the life span and/or to increase the activity of natural killer cells (NK cells) in a living being, preferably in humans, comprising the following steps: (1) provision of the composition according to the invention, and (2) administration of the composition into or to the living being, and (3) optionally repetition of steps (1) and (2), wherein preferably the administration is systemically and/or topically.

The features, characteristics and advantages of the composition according to the invention apply likewise to the use according to the invention and the method according to the invention.

It goes without saying that the features mentioned before and those to be mentioned in the following cannot only be used in the respective indicated combination but also in other combinations or in isolated position without departing from the scope of the invention.

The invention is now explained in more detail by means of embodiments which result in further features, characteristics and advantages. The embodiments should illustrate the invention, however do not restrict its scope. There, reference is made to the enclosed figures.

BRIEF DESCRIPTION OF THE DRAWINGS

FIG. 8 6-PN and 8-PN increase the metabolic activity of PBMCs of healthy donors or the standardized, commercial NK cell line NKL, measured with the Promega CellTiter Blue Assay. (A) PBMCs of two healthy donors were one time treated with 12.5 µM or 25 µM of 6-PN or 8-PN and examined after 48 hours. (B) NKL cells were one time treated with 12.5 µM or 25 µM of 6-PN or 8-PN and examined after 48 h.

DESCRIPTION OF PREFERRED EMBODIMENTS

1. Synthesis of 6-prenylnaringinin and 8-prenylnaringinin (PN)

8-prenylnaringinin and 6-prenylnaringinin were synthesized according to Gester et al. (2001), An efficient synthesis of the potent phytoestrogens 8-prenylnaringenin and 6-(1,1-dimethylallyl)naringenin by europium (111)-catalyzed Claisen rearrangement, Tetrahedron 57, 1015-1018 and Tischer and Metz (2007), Selective C-6 prenylation of flavonoids via europium(III)-catalyzed Claisen rearrangement and cross-metathesis, Advanced Synthesis & Catalysis 349, 147-151. The content of both of the afore publications is incorporated into the present application by reference.

2. Increased Viability of Human NK Cells by 6-PN and 8-PN

Figure 1:
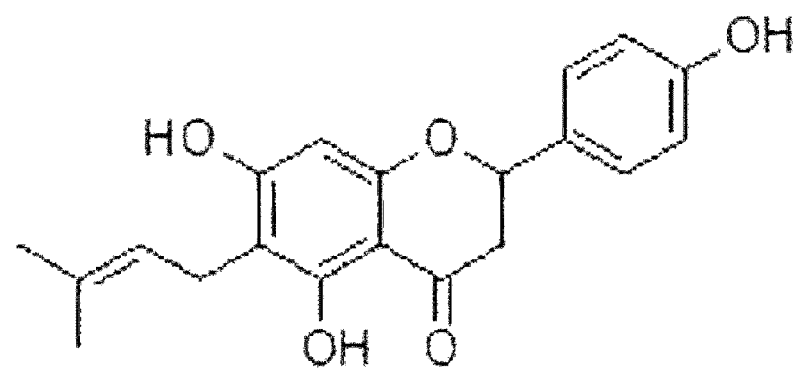
FIG. 1 chemical structures of (A) 6-PN and (B) 8-PN. Shown are the chemical structures of 6-prenylnaringenin (5,6-dihydroxy-2-(4-hydroxy-phenyl)-6-(3-methyl-but-2-enyl)-chroman-4-one) and 8-prenylnaringenin (5,7-dihydroxy-2-(4-hydroxy-phenyl)-8-(3-methyl-but-2-enyl)-chroman-4-one).
Figure 1:
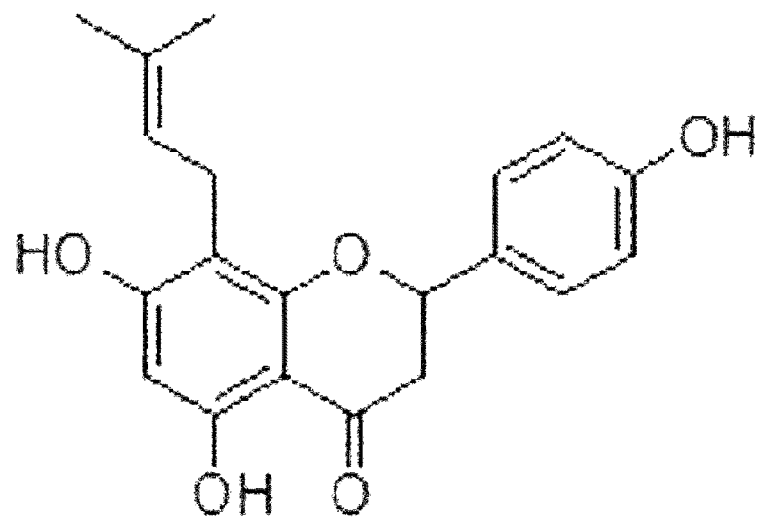
Figure 2:
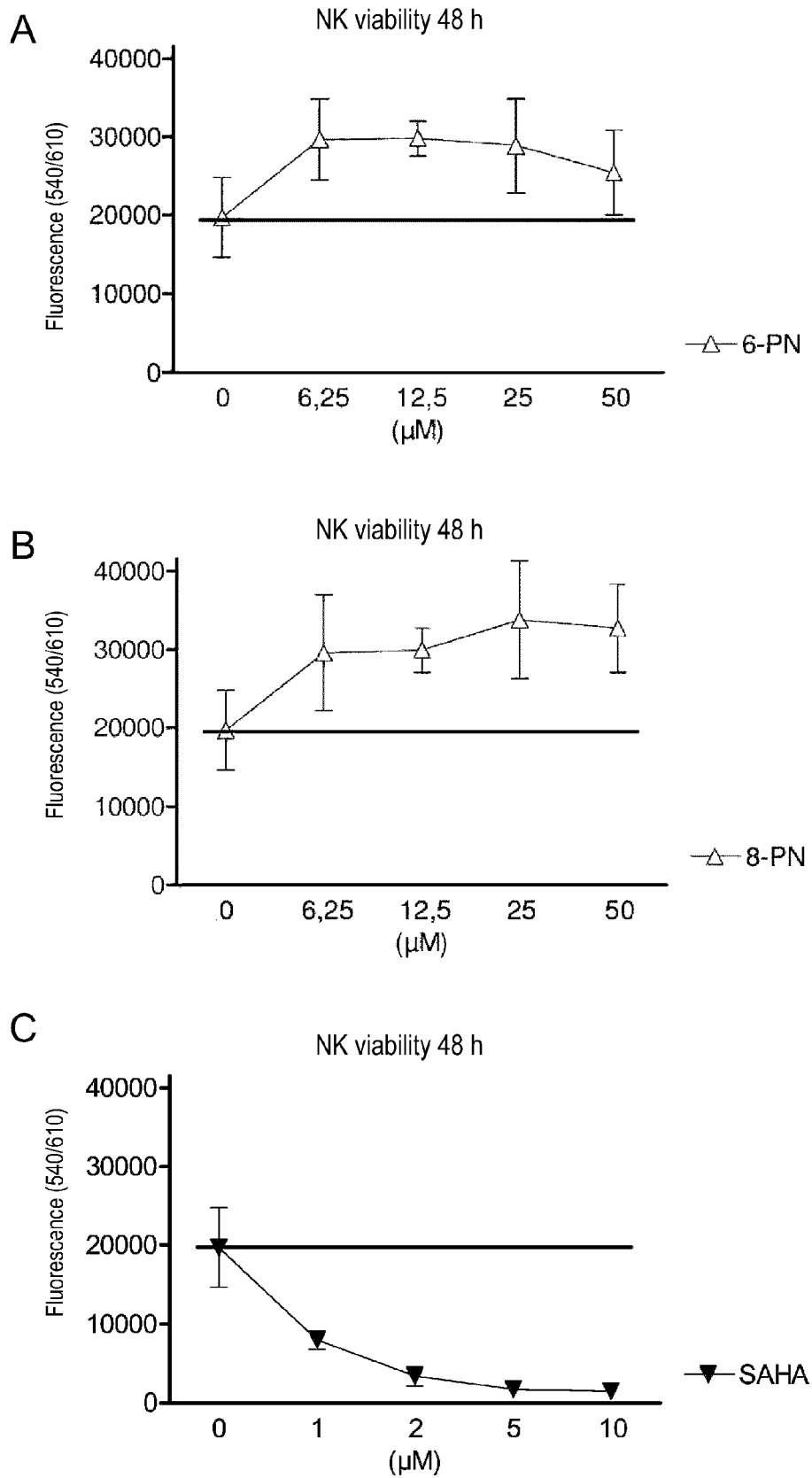
FIG. 2 Viability measurements on NK cells 48 hours after the treatment with different concentrations of (A) 6-PN, (B) 8-PN, or (C) SAHA.

Human NK cells were treated for 48 hours with 6.25, 12.5, 25 or 50 µM of 6-PN or 8-PN. In the following a viability measurement was carried out (CellTiterBlue Viability Asasy, Promega, Madison, United States of America). The clinically used and established HDACi SAHA (Vorinostat) was used in low concentrations as a reference die for both natural HDACi 6-PN and 8-PN. The result is shown in the FIG. 2. Shown are the mean values with a standard deviation from three independent experiments with expanded NK cells from three healthy human donors. The horizontal continuous line visualizes the value of the untreated control; a decrease of the fluorescence signal means a reduction of the viability. It can be shown that in concentration areas between 6.25 and 50 µM a in parts significant increase of the viability of human NK cells in contrast to the control sample and the SAHA treated cells can be measured. The SAHA treatment group shows, in contrast, over the entire concentration range a significant decrease of the viability of the NK cells (FIG. 2C).

3. Extended Overall Survival of Human NK Cells

Figure 3:
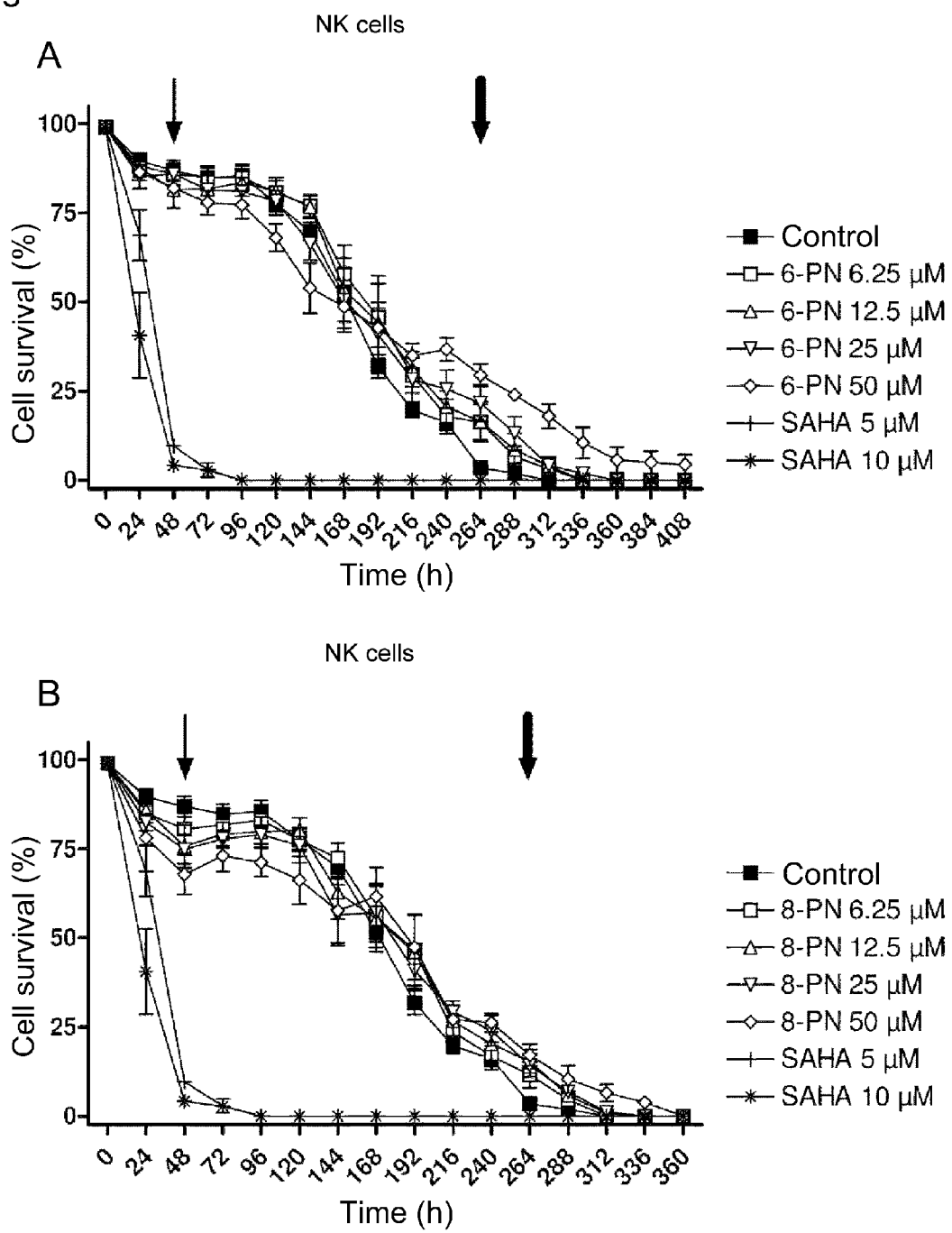
FIG. 3 Measurement of the overall survival of NK cells after a one time treatment with different concentrations of (A) 6-PN or SAHA or (B) 8-PN or SAHA.

Human NK cells were treated with 6.25, 12.5, 25 or 50 µM of 6-PN or 8-PN. Subsequently via a tryptan blue staining and a daily microscopic counting in standardized C chip counter chambers the overall survival of NK cells was measured. As a reference dye again the HDACi SAHA (Vorinostat) was used. The result is shown in the FIG. 3. Shown is the average value with standard deviation from three independent experiments with expanded NK cells from three healthy human donors. The left arrow visualizes <10% of living cells in the SAHA treatment group; the right arrow visualizes <10% of living cells in the untreated control group. There it is shown that the survival rate of the NK cells over all of the tested concentrations of 6-PN (FIG. 3A) and 8-PN (FIG. 3B) is significantly increased over the untreated control and the SAHA treated cells.

4. Increased Activity of Human NK Cells on Human Tumor Cells

Figure 4:
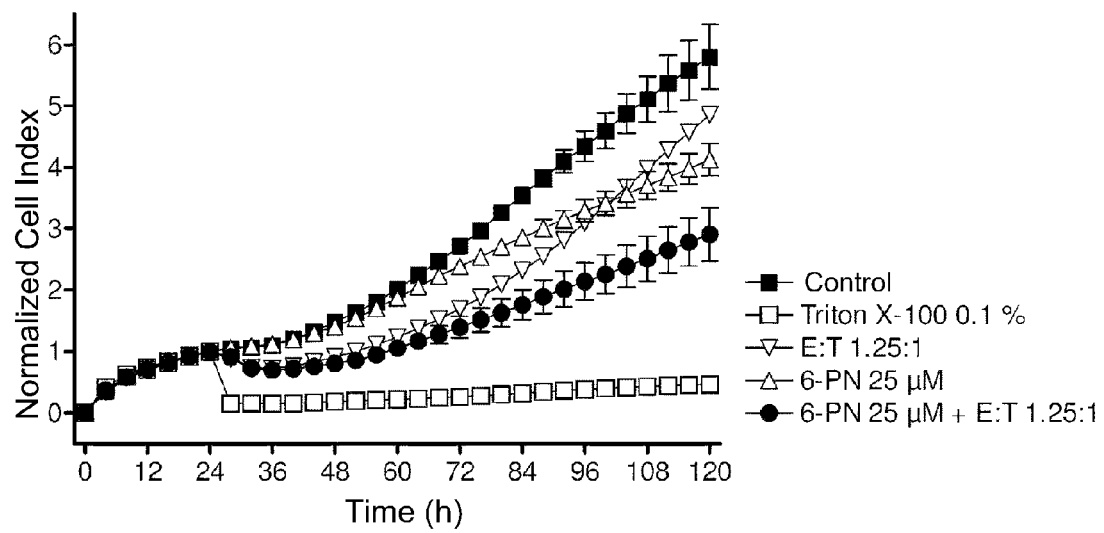
FIG. 4 (A)-(D) Analysis of the activity of NK cells on human HepG2 tumor cells.
Figure 4:
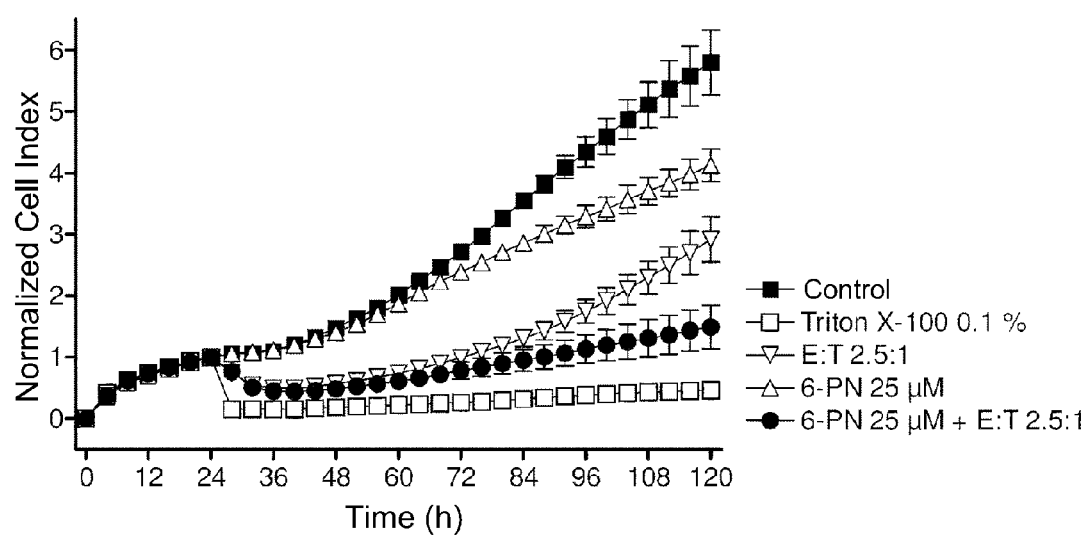
Figure 4:
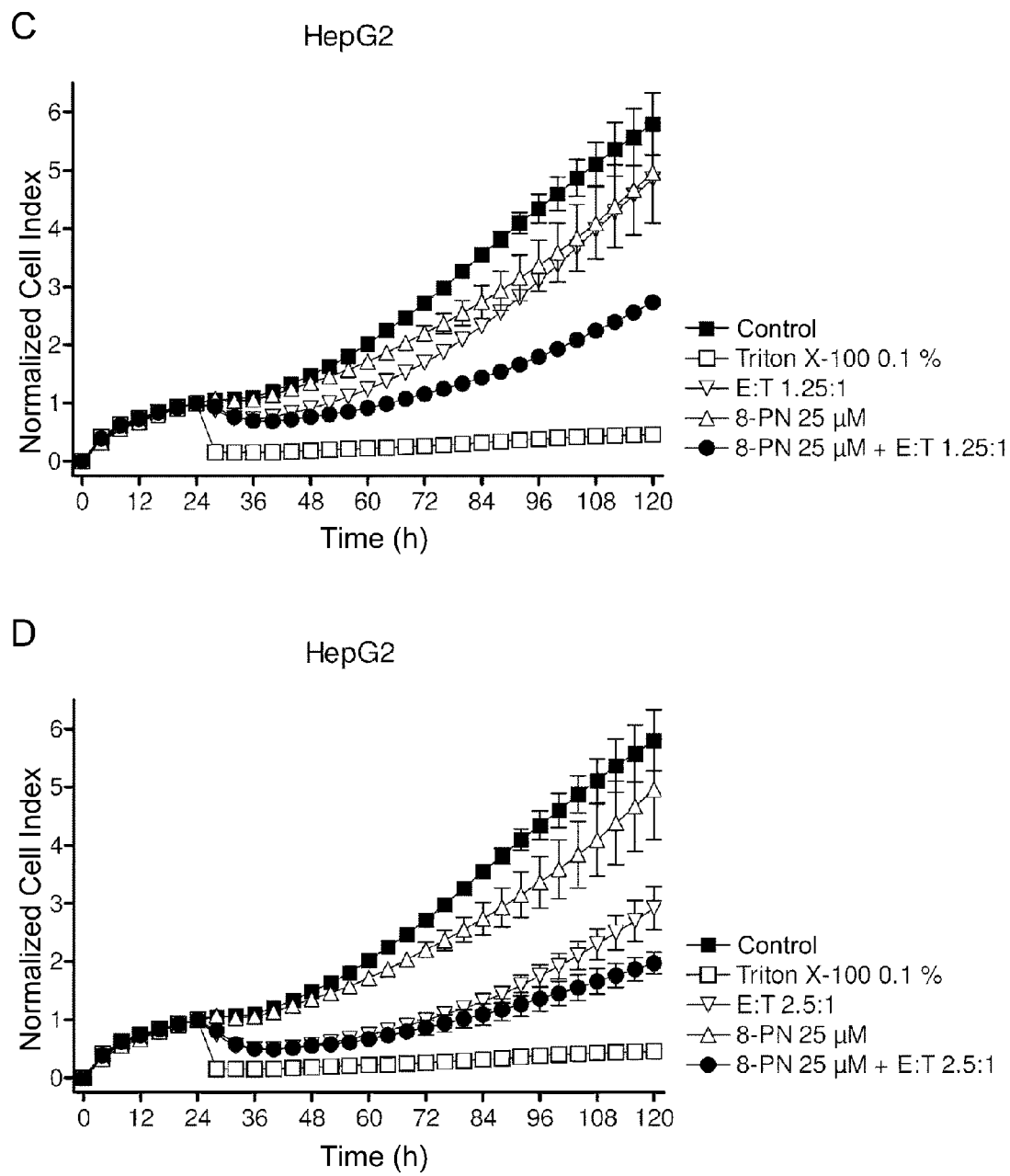

In a further experiment the NK activity on human hepG2 tumor cells by means of realtime cell monitoring (Roche Applied Sciences xCELLigence SP-System, Mannheim, Germany) was analyzed. HepG2 tumor cells are characterized by a low sensitivity against 6-PN or 8-PN, respectively. The cellular impedance of the adherent tumor cells were measured as parameters for the cell status (cell number, viability, morphology, adhesion). As a positive control for the induction of cell death Triton X-100 was used. Three independent experiments with expanded NK cells from three healthy human donors were carried out. The result is shown in the FIG. 4. Shown are the average values with standard deviation of one exemplary experiment. The HepG2 tumor cells (target) were incubated at the start of the treatment (24 hours) with 25 µM of 6-PN or 8-PN or with NK cells (effector) (effector to target ratio (E:T)=1.25:1 or 2.5:1) or with the combination of HDACi and NK cells. The normalization happened at the start of the treatment and a decrease of the impedance (normalized cell index) means a reduction of the cell viability or the cell status, respectively. There it can be shown in comparison to the control for the induced cell death (Triton X-100) that both in a treatment with 6-PN (FIG. 4A, B) as well as 8-PN (FIG. 4C, D) an increased activity of the human NK cells over human tumor cells does occur. Experiments with other concentrations of 6-PN or 8-PN (e.g. 6.25 µM) or another E:T ratio (e.g. 5:1) as well as a further tumor cell line (e.g. Hep3B) showed equivalent results.

Figure 5:
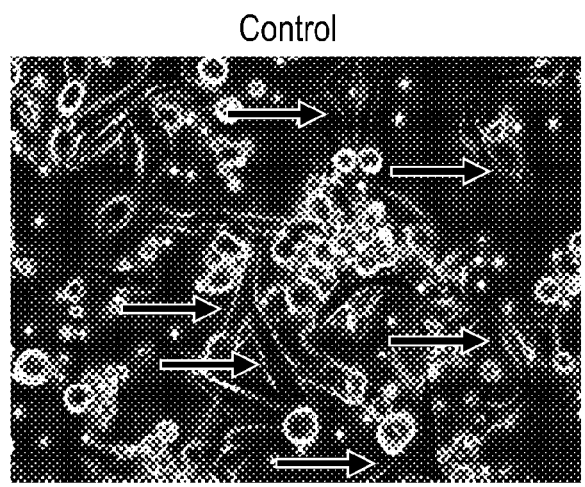
FIG. 5 6-PN and 8-PN activate primary human immune cells and reduce the tumor mass of a metastasizing malignant melanoma. (A) microscopic images in 200× magnification, which show melanoma tumor cells with adherent immune cells; after a treatment with 12.5 µM or 25 µM of 6-PN or 8-PN the number of vital tumor cells is significantly reduced (arrows). (B) Quantitative evaluation of the tumor cells 48, 72, and 96 hours after the start of the treatment FIG. 6 (A) 6-PN and (B) 8-PN increase/extend the viability of NK cells of healthy donors measured in an automated viability/cell counter device.
Figure 5:
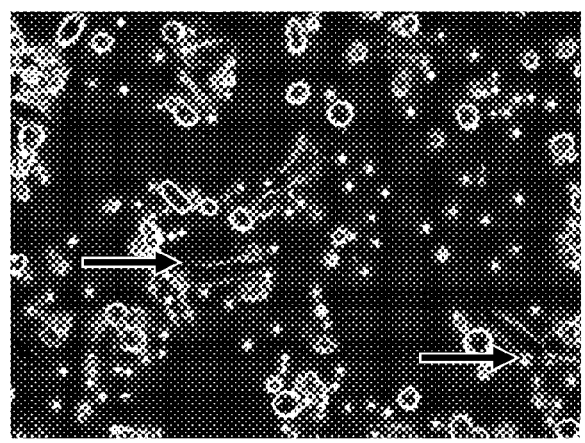
Figure 5:
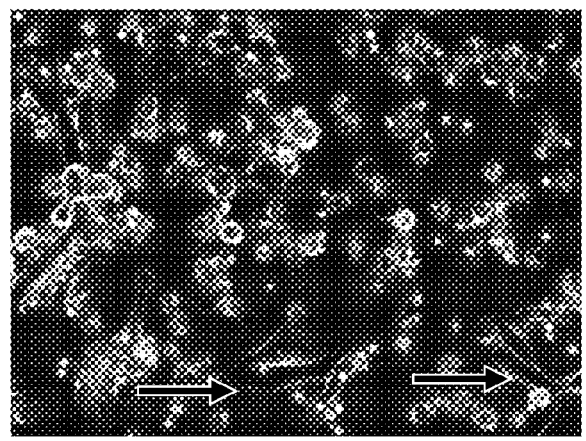
Figure 5:
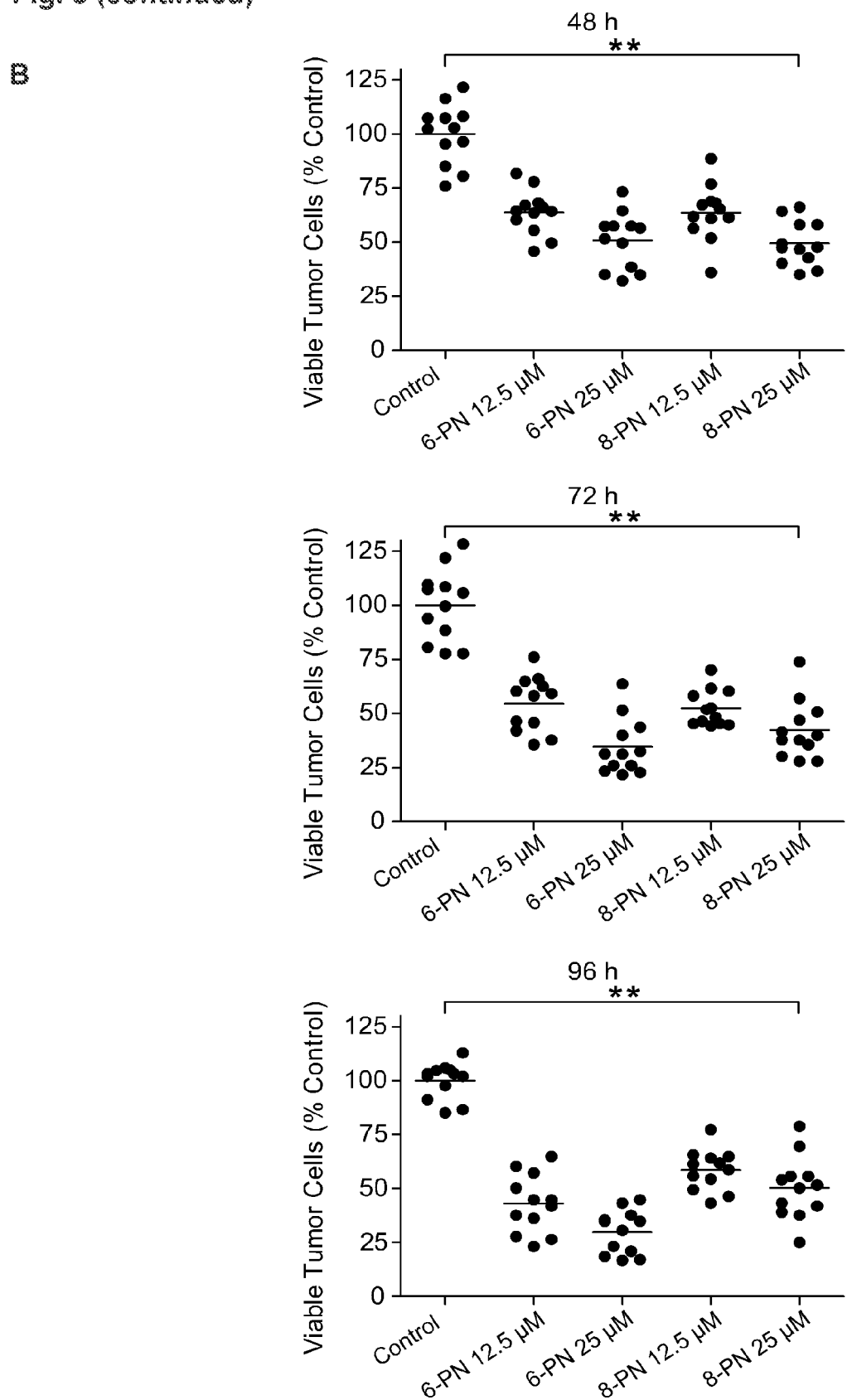

5. Confirmation of the Antitumor Immunomodulation by Means of Primary Patient Material In a further experiment with primary patient material it was demonstrated that 6-PN and 8-PN activate primary human immune cells and reduce the tumor mass of a metastasing malign melanoma. The result of this experiment is shown in the FIG. 5: A microscopic images in 200× magnification, which show the melanoma tumor cells with adherent immune cells; after a treatment with 12.5 µM or 25 µM of 6-PN or 8-PN the number of vital tumor cells is significantly reduced (red arrows). B The quantitative evaluation of the tumor cells 48, 72, and 96 hours after the start of the treatment shows a significant decrease of the melanoma cells under the treatment with 12.5 µM or 25 µM of 6-PN or 8-PN, respectively; three independent counts in triplicates; one-way ANOVA Dunnetts multiple comparison test, **$P<0.01$.

Figure 6:
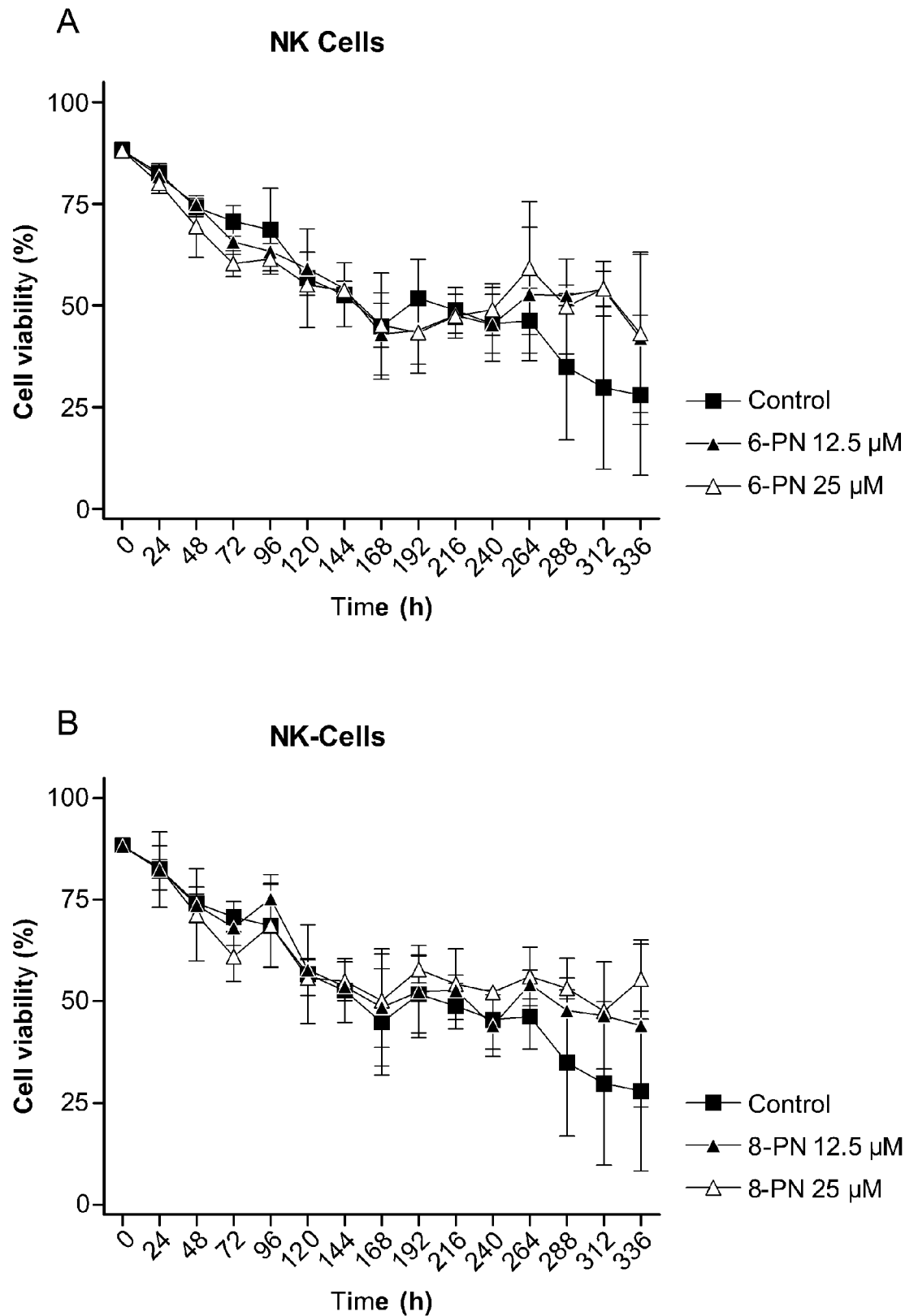

6. Confirmation of the Previous Increase of the NK Cell Viability With Automatic Cell Counting Device In a subsequent experiment it was shown that 6-PN and 8-PN increase/extend the viability of NK cells of healthy donors, measured in an automated viability/cell counting device. The examination therefore is independent from the experimentator. The result is shown in the FIG. 6. NK cells of two healthy donors were one time treated with 12.5 µM or 25 µM of 6-PN or 8-PN, respectively, and subsequently two independent points in time on a daily basis examined by means of a nucleo counter NC-250 cell counting device with respect to viability over a time period of 336 h; shown is the average value +/−SD.

7. Extension of the Increase in Viability to the Higher-Level Cell Population: Peripheral Blood Mononuclear Cells (PBMCs)

Figure 7:
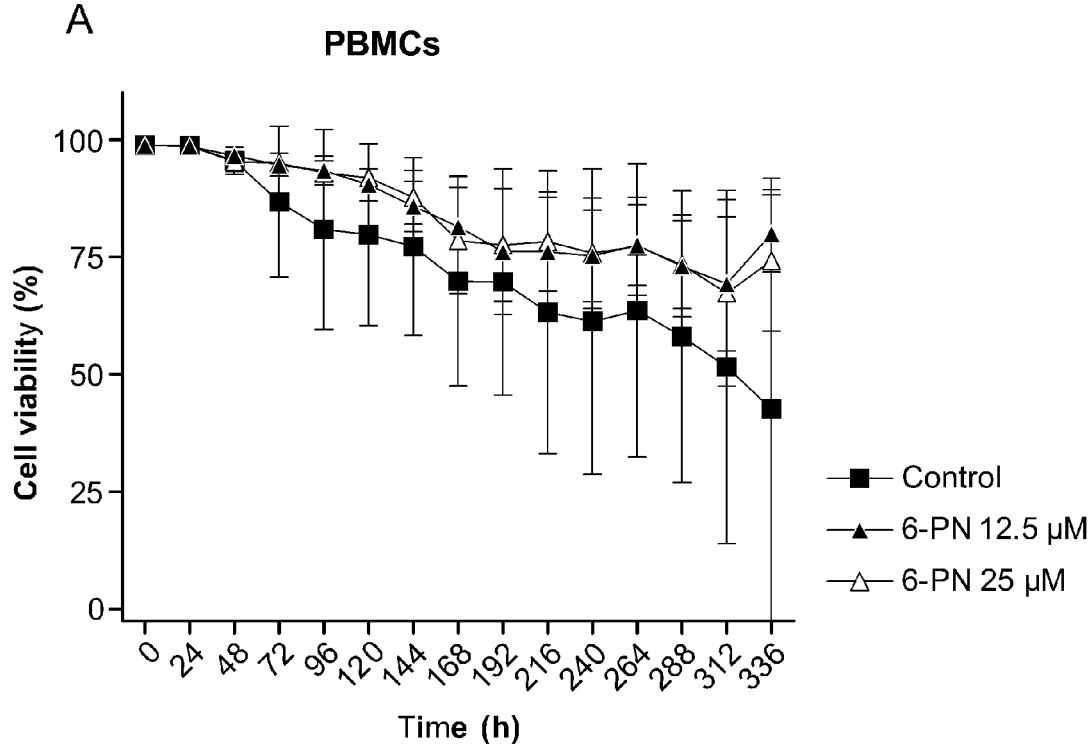
FIG. 7 (A) 6-PN and (B) 8-PN increase/extend the viability of PBMCs of healthy donors measured in an automated viability/cell counter device.
Figure 7:
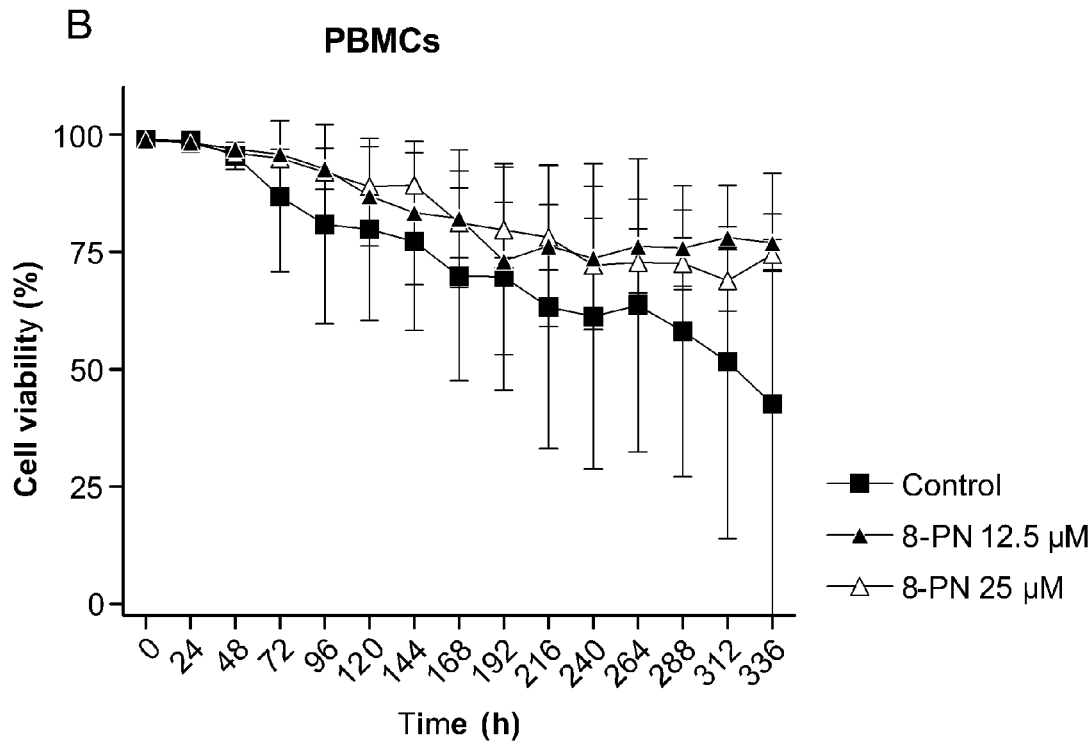

In a further experiment it was shown that 6-PN and 8-PN increase/extend viability of PBMCs of healthy donors, measured in an automated viability/cell counting device. The result is shown in the FIG. 7: PBMCs of three healthy donors were one time treated with 12.5 µM or 25 µM of 6-PN or 8-PN and subsequently on a daily basis at independent points in time examined by means of a nucleo counter NC-250 cell counting device with respect to viability over a time period of 336 hours; shown is the average value +/−SD.

8. Confirmation of the Activating Activity on PBMCs by Means of an Alternative Assay and Repeated Confirmation by Means of a Commercial NK Cell Line (NKL)

Figure 8:
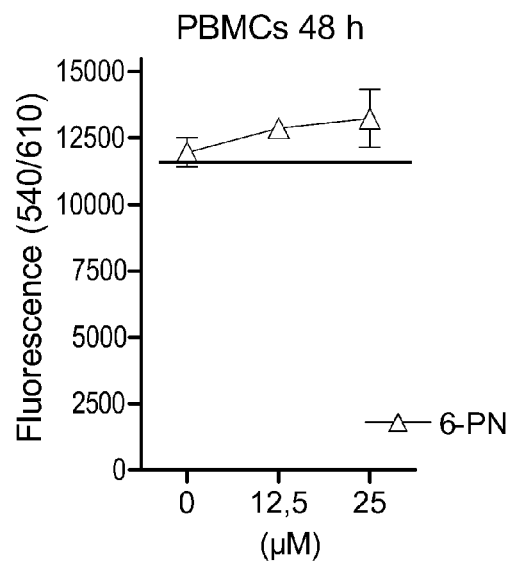
Figure 8:
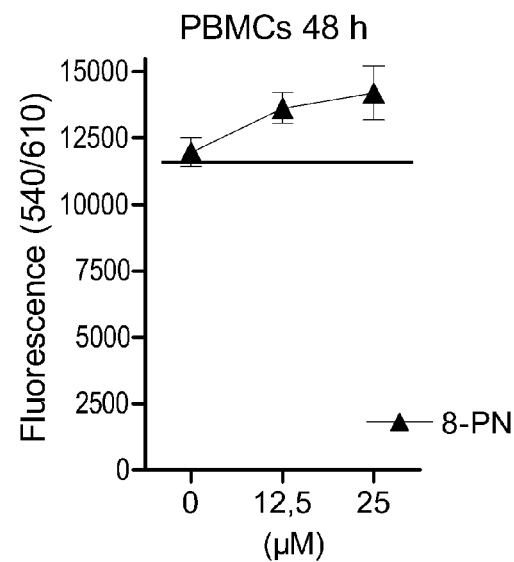
Figure 8:
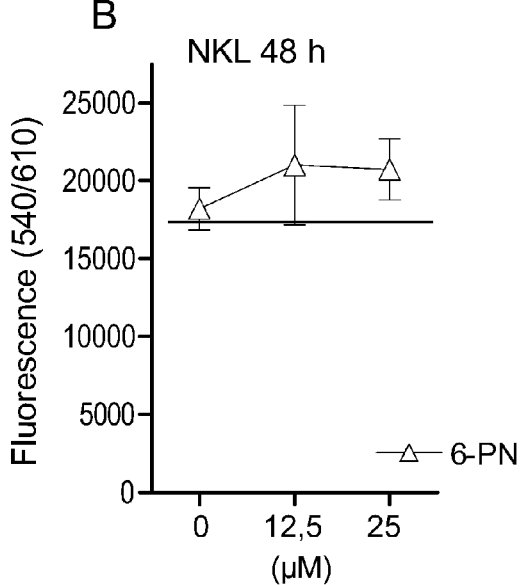
Figure 8:
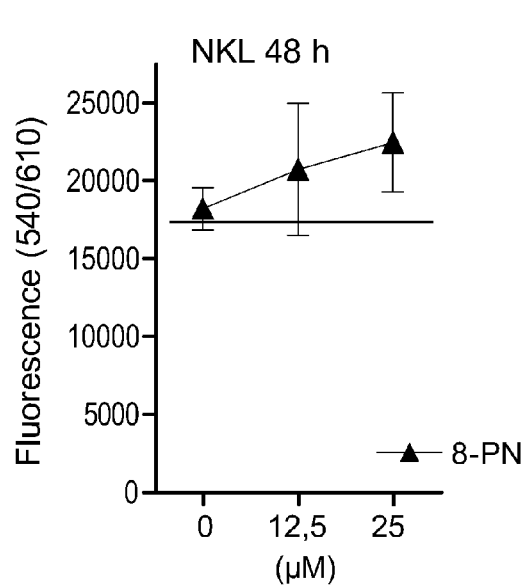

In another experiment it was shown that 6-PN and 8-PN increase the metabolic activity of PBMCs of healthy donors or the standardized commercial NK cell line NKL, measured with the Promega CellTiter-Blue Assay. The result is shown in the FIG. 8: A PBMCs of two healthy donors were one time treated with 12.5 µM or 25 µM of 6-PN or 8-PN and examined after 48 hours. B NKL cells were one time treated with 12.5 µM or 25 µM of 6-PN or 8-PN and examined after 48 h. In both immune cell populations and in both treatments an increase of a metabolic activity can be detected; shown is the average value +/−SD.

CONCLUSION

The inventors were able to demonstrate by means of 6-prenylnaringinin (6-PN) and 8-prenylnaringinin (8-PN) that prenylflavonoids exert immunomodulatory effects on the innate immune system or NK cells, respectively. These natural HDACi (i) increase massively the viability of NK cells, (ii) extend the overall survival of NK cells and (iii) activate NK cells or effect an increased "killing" of human abnormal or infected cells by NK cells.

What is claimed is:

1. A method of immunomodulation in a living being in need thereof comprising administering 6-prenylnaringinin and/or 8-prenylnaringinin into the living being.

2. The method of claim 1, wherein the immunomodulation is an immunostimulation.

3. The method of claim 1, wherein the immunomodulation is an immunomodulation of the inert immune system.

4. The method of claim 1, wherein the immunomodulation results in an effect on natural killer cells (NK cells) selected from the group consisting of: stimulation of the viability, increase of the viability, increase of the life span, increase of the activity.

5. The method of claim 1, wherein said 6-prenylnaringinin and/or 8-prenylnaringinin is administered as a pharmaceutical composition.

6. The method of claim 5 for the treatment of a disease which is selected from the group consisting of: viral infections, autoimmune diseases, tumor diseases.

7. The method of claim 1, which wherein said 6-prenylnaringinin and/or 8-prenylnaringinin is administered as a food product.

8. The method of claim 7, wherein it is a food product on the basis of hops.

9. The method of claim 1, wherein said 6-prenylnaringinin and/or 8-prenylnaringinin is present in micelled form.

10. The method of claim 1, wherein the administering of said 6-prenylnaringinin and/or 8-prenylnaringinin is repeated.

11. The method of claim 1, wherein the administering of said 6-prenylnaringinin and/or 8-prenylnaringinin is done administration occurs systemically and/or topically.

* * * * *

UNITED STATES PATENT AND TRADEMARK OFFICE
CERTIFICATE OF CORRECTION

PATENT NO. : 9,855,242 B2
APPLICATION NO. : 15/130556
DATED : January 2, 2018
INVENTOR(S) : Christian Busch et al.

It is certified that error appears in the above-identified patent and that said Letters Patent is hereby corrected as shown below:

On the Title Page

Item (73), (Assignee) at Line 1, change "UNIVERITÄT" to --UNIVERSITÄT--.

In Column 2 (item (56)) at Line 38, Under Other Publications, change "6(" to --6-(--.

In the Drawings

At sheet 2 of 10 (Fig. 2) at Line 7 (approx.), change "6,25" to --6.25--.

At sheet 2 of 10 (Fig. 2) at Line 7 (approx.), change "12,5" to --12.5--.

At sheet 2 of 10 (Fig. 2) at Line 15 (approx.), change "6,25" to --6.25--.

At sheet 2 of 10 (Fig. 2) at Line 15 (approx.), change "12,5" to --12.5--.

At sheet 10 of 10 (Fig. 8) at Line 10 (approx., Graph 1, A), change "12,5" to --12.5--.

At sheet 10 of 10 (Fig. 8) at Line 10 (approx., Graph 2, A), change "12,5" to --12.5--.

At sheet 10 of 10 (Fig. 8) at Line 20 (approx., Graph 1, B), change "12,5" to --12.5--.

At sheet 10 of 10 (Fig. 8) at Line 20 (approx., Graph 2, B), change "12,5" to --12.5--.

In the Specification

In Column 1 at Line 11 (approx.), change "15 Oct." to --16 Oct.--.

In Column 2 at Line 7, change "flavonones," to --flavanones,--.

Signed and Sealed this
Ninth Day of April, 2019

Andrei Iancu
*Director of the United States Patent and Trademark Office*

CERTIFICATE OF CORRECTION (continued)
U.S. Pat. No. 9,855,242 B2

In Column 2 at Lines 8-9, change "defensce" to --defense--.

In Column 2 at Line 35, change "enatiomeres" to --enantiomers--.

In Column 2 at Line 51, change "phytoestogen," to --phytoestrogen,--.

In Column 2 at Line 53, change "immitates" to --imitates--.

In Column 3 at Line 14 (approx.), change "Antiproliferative" to --Anti-proliferative--.

In Column 5 at Line 64, after "treatment" insert --.--.

In Column 6 at Line 32, change "Asasy," to --Assay,--.

In Column 7 at Line 21, change "(FIG. 4A," to --(FIGS. 4A,--.

In Column 7 at Line 21, change "(FIG. 4C," to --(FIGS. 4C,--.

In Column 7 at Line 32, change "metastasing malign" to --metastasizing malignant--.

In the Claims

In Column 8 at Line 50 (approx.), in Claim 7, before "wherein" delete "which".

In Column 8 at Line 62, in Claim 11, before "systemically" delete "administration occurs".